United States Patent [19]
Bennett et al.

[11] Patent Number: 5,625,125
[45] Date of Patent: Apr. 29, 1997

[54] PHOSPHOLIPASE A₂ EXPRESSING TRANSGENIC ANIMALS

[75] Inventors: C. Frank Bennett, Carlsbad, Calif.; David S. Grass, Lawrenceville; Mark E. Swanson, Princeton Junction, both of N.J.

[73] Assignee: DNX Biotherapeutics, Princeton, N.J.

[21] Appl. No.: 287,980

[22] Filed: Aug. 9, 1994

[51] Int. Cl.⁶ .............................. C12N 5/00; C12N 15/00; G01N 33/48
[52] U.S. Cl. .................. 800/2; 800/DIG. 1; 424/9.1; 424/9.2; 435/172.3
[58] Field of Search ................................. 800/2, DIG. 1; 424/9, 9.1, 9.2; 435/172.3; 536/23.2, 23.5

[56] References Cited

PUBLICATIONS

Kramer et al (1989) J Biol Chem 264: 5768–5775.
Merlino (1991) FASEB J 5: 2996–3001.
Bereziat et al (1990) J Lipid Mediators 2:159–172.
Strojek et al (1988) Genetic Engineering: Principles and Methods 10: 221–246.
Lang, R.A., et al., 1987, Cell 51:675–686.
Shull, M.M., et al., 1992, Nature 359:693–699.
Turksen, K., et al., 1992, Proc. Natl. Acad. Sci. 89:5068–72.
Vassar, R. & Fuchs, E., 1991, Genes & Development 5:714–727.
Keffer, J., et al., 1991, EMBO J. 10:4025–31.
Tepper, R.I., et al., 1990, Cell 62:457–677.
Lewis, D.B., et al., 1992, J. Bone & Min. Res. 7:(51) PS97.
Dent, L.A., 1990, J. Exp. Med. 172:1425.
Wogensen, L., et al., 1994, J. Interferon Res. 14:111–114.
Taverne, J., 1993, Int. J. Exp. Path. 74:525–546.
J. Cell Biochem Suppl., #17, Part B, 1993, p. 92, Abstract E329.
Toyonaga, T., et al., 1994, Proc. Natl. Acad. Sci. USA, 91:614–618.
Taverne, J., 1994, Parasitology Today, vol. 10, No. 7, pp. 258–262.
J. Cell Biochem Suppl., #18, Part A, 1994, p. 283, Abstract E303.
The Journal of Investigative Dermatology, vol. 102, #4, 1994, p. 556, Abstract 195.

Primary Examiner—Bruce R. Campell
Attorney, Agent, or Firm—Pennie & Edmonds

[57] ABSTRACT

The present invention concerns transgenic animals that express an abnormaly high level of phospholipase A₂ in their serum, liver, lung, kidney and skin. More particularly rats and mice expressing human non-pancreatic, low molecular weight phospholipase A₂ are disclosed. Although transfected with a normal human gene, the animals develop a variety of pathological signs and produce the enzyme ectopically. The animals of the invention are useful for the testing of compounds to determine whether the compounds possess in vivo activity as phospholipase inhibitors or antagonists suitable for pharmacolgic use.

10 Claims, 6 Drawing Sheets

PHOSPHOLIPASE A₂ EXPRESSING TRANSGENIC ANIMALS

1. FIELD OF THE INVENTION

This invention concerns the field of transgenic animals that are useful in the pharmacologic and medicinal chemistry arts. More particularly, the invention concerns a non-human animal having inserted and expressing the human type II Phospholipase $A_2$ gene. This gene encodes an enzyme that catalyzes the initial, rate-limiting step in the synthesis of eicosanoids, which include major mediators of inflammation, and also of Platelet Activating Factor, which is a potent initiator of thrombus formation. The transgenic animal of the invention provides a heretofore unavailable means to test the effects of compounds which are potential modulators of the synthesis of these mediators of inflammation, especially of drugs that act as inhibitors or antagonists of Phospholipase $A_2$.

2. BACKGROUND TO THE INVENTION

2.1 Phospholipase $A_2$ Proteins

Phospholipase A2s (PLA2s) are enzymes that catalyze the hydrolysis of the sn-2 fatty acyl ester bond of membrane phospholipids to yield a free fatty acid, e.g., arachidonic acid and a lysophospholipid. Both the arachidonic acid and the lysophospholipids can be further metabolized to produce inflammatory mediators. The products of arachidonic acid metabolism are eicosanoids: lipoxin, HETES, leukotrienes and prostaglandins. Leukotrienes recruit inflammatory cells and promote extravasation of these cells into injured sites and promote epidermal proliferation. Leukotrienes also stimulate the release of superoxide and proteases that damage tissue at an inflamed site. Prostaglandins increase blood flow allowing infiltration of leukocytes to inflamed sites and potentiate the pain response. The 2-acetyl derivative of 1-O-alkyl-glycero-3-phosphocholine lysophospholipid metabolism is Platelet Activating Factor (PAF). PAF causes aggregation of platelets, neutrophils, and monocytes and is also a very potent eosinophilic chemotactic factor.

There are three types of PLA2 proteins in mammals including humans. There is a cytoplasmic PLA2 having a molecular weight of about 85 KD. There is also a class of closely related low molecular weight PLA2 proteins. Low molecular weight PLA2s are characterized by a millimolar catalytic requirement for calcium and a rigid three dimensional structure maintained by multiple disulfide bridges. These proteins, which have a uniform molecular weight of 14 KD and contain an invariable 18 amino acids sequence. The low molecular weight phospholipases can be divided into two groups based on their amino acid sequence. Waite, M., 1987, 5 THE PHOSPHOLIPASES, HANDBOOK OF LIPID RESEARCH, ed. by D. J. Hanahan (Plenum Press, NY) pp 155–190. Type I PLA2 include mammalian pancreatic digestive enzymes find the well characterized snake venom enzymes. The type I enzyme has a disulfide bridge connecting cysteines at positions 11 and 77.

Type II PLA2s lack the disulfide bridge between positions 11 and 77 and have a carboxyl terminal 6 amino acid extension. Type II PLA2s share 30–40% amino acid sequence homology with each other. The purified human type II PLA2 enzyme is significantly more potent generator of inflammation that the type I PLA2 enzyme found in pancreas. Mammalian type II PLA2s are normally present in trace amounts in many different tissues and cell types, such as platelets, neutrophils, vascular smooth muscle cells, spleen, liver, and intestine as well as placenta. Type II PLA2s are secreted by certain cells of the immune system in response to stimulation. This type of PLA2 is found in soluble form at inflammatory sites, e.g., experimental casein or glycogen-induced peritoneal exudates, Forst, J. M., et al., 1986, BIOCHEMISTRY 25: 8381–8385; Chang, J., et al., 1987, BIOCHEM. PHARMACOL., 36: 2429–2436, and the synovial fluid of patients with rheumatoid arthritis, Vadas, P., et al., 1985, LIFE SCI. 36: 579–587; Seilhamer, J. J., et al., 1989, J. BIOL CHEM. 264: 5335–5338, Kramer, R. M., et al., 1989, J. BIOL. CHEM. 264: 5768–5775. Recombinantly produced type II PLA2 is arthritogenic when injected into the joint space of a rabbit. Bomalaski, J. S., et al., 1991, J. IMMUNOL. 146: 3904–3910. Disease conditions in man such as acute pancreatitis, septic shock, inflammatory arthritis and adult respiratory distress syndrome (ARDS), have been associated with elevated levels of secretory PLA2s. Vadas, P., & Pruzanski, W., 1986, LABORATORY INVESTIGATION 55:391–404.

These data have led to a generally recognized need for a clinically effective inhibitor of type II PLA2 enzyme activity. Garst, M. E., 1992, CURR. OPIN. THERA. PATENTS 2:400–408. See, e.g., Miyake, A., et al., 1992, J. OF PHARM. EXP. THERA. 263:1302–1307; Kreft, A., 1993, AGENTS ACTIONS 39:C33–C35.

2.2 Techniques of Detecting Phospholipase $A_2$ Activity and its Antagonists or Inhibitors The standard, presently available technique that researchers use to detect PLA2 inhibitors is based on the reaction, in vitro, of a purified enzyme or enzyme-containing extract, e.g., a platelet extract, and a radiolabelled substrate, e.g., a $C^{14}$-oleic acid labeled phospholipid. After a time the reaction is stopped, the substrate and products are extracted, fractionated and the label present in the substrate and product fractions are determined to measure the enzyme activity. Although such an assay is useful to obtain an indication of the relative strengths of different inhibitors, such an assay is not able to accurately predict the effects that that potential antagonist or inhibitor will display in vivo in an inflammatory setting, nor predict whether the test compound will display unacceptable side-effects such as, for example, blocking other essential enzyme activities.

One common alternative to the above noted in vitro tests is to induce, in experimental animals, an inflammatory response and to coordinately administer a test compound that is a potential PLA2 antagonist or inhibitor. The comparison of the experimental animals that have and have not received the test compound can be used as a measure of efficacy of the test compound. The shortcomings of the in vitro approach are two fold. Firstly, the experimental manipulation is, itself, an independent source of variation, that potentially obscures the test results. Secondly, experimental models such as adjuvant arthritis, Pearson, C.M., 1964, ARTHRITIS RHEUM. 7: 80, or λ-carrageenan paw edema, Otterness, I.V., et alia., 1988, METHODS IN ENZYMOLOGY 162: 320–327, are complex responses to a generalized insult. The host response to the insult is mediated through a variety of different pathways.

Thus, for example, it has long been known that the anti-inflammatory glucocorticoids induce the production of proteins that are directly inhibitory to PLA2. Hong, S. L., & Levine, L., 1876, J.BIOL.CHEM. 251: 5814–16; Pepinsky, R. B., 1986, J.BIOL.CHEM. 261: 4239–4246; Wallner, B. P. et al., 1986, NATURE 320: 77–81; Suwa, Y., et al., 1990, PROC. NATL. ACAD. SCI. 87: 2395–99. However, because of the complexity of the inflammatory response and the multiplicity of relevant pathways that are affected by glucocorticoids, it is not possible to determine what portion of the effects of glucocorticoids are due to their anti-PLA2 activity.

Lastly, experimental animal models are, of course, dependent upon the PLA2 of the host, which is not identical to human PLA2 and which may respond differently to the test compound. For example, the homology between human and rat type II PLA2 is about 70% at the amino acid level. A more extensive comparison of PLA2's may be found in Davidson, E. F. & Dennis, E. A., 1990, J.MOL.EVOL. 31: 228. Thus, in such situations the finding that a test compound may have a significant anti-inflammatory effect could not, without further study, lead to the interpretation that the anti-inflammatory effects of the test compound are mediated by the inhibition of PLA2 activity nor that such effects would be available in clinical usage.

There is, then, a need for an in vivo experimental system that displays a pure human PLA2 mediated pathology with minimal experimental manipulation. Such an experimental system could be used to evaluate, in vivo, the efficacy of a test compound as a potential antagonist or inhibitor of PLA2.

3. SUMMARY OF THE INVENTION

The present invention relates to transgenic animals be expressing an abnormally high level of a type II Phospholipase $A_2$. Such animals can be used in the identification and the characterization of compounds as potential antagonists or inhibitors for use in medicine. Such compounds can be of two types, those that directly inhibit the activity of existing PLA2 protein (inhibitors) and those that block the synthesis or activity of the PLA2 protein by binding to a molecule other than PLA2 (antagonists).

In a preferred embodiment, the type II phospholipase is human non-pancreatic phospholipase and the animal is a rodent. The invention is based on the unexpected discovery that transgenic mice and rats that have had one or several copies of the human non-pancreatic type II PLA2 (hereinafter "hnp-II-PLA2") gene incorporated into their genome both express the gene and are viable and, hence, these animals display enhanced levels of phospholipase activity in their serum and in a variety of their tissues.

A further unexpected aspect of the invention is that these animals develop gross signs of the over-expression of PLA2: severe alopecia, epidermal and adnexal hyperplasia. Although these human type II phospholipase A2 transgenic mice and rats are runted during development, they spontaneously recover to normal body weights and the mice are able to breed successfully and transmit the transgene to their offspring.

5. DETAILED DESCRIPTION OF THE INVENTION

5.1 Isolation and Characteristics of the Human Non-Pancreatic Phospholipase $A_2$ Gene There are at least two genes encoding human Type II PLA2 enzymes. The more prevalent type, which is present in placenta, platelets and rheumatoid synovial fluid and is usually referred to as non-pancreatic type II PLA2, hereinafter "hnp-II-PLA2," has been previously cloned, sequenced and characterized, Kramer, R. M., et al., 1989, J. BIOL. CHEM. 264: 5768–5775, FIG. 3 (which sequence is hereby incorporated by reference). The sequence of hnp-II-PLA2 is also available as GENBANK/J04705. More recently, a second low molecular weight, non-pancreatic human PLA2 has been identified, which is expressed most strongly in heart and placenta. This gene is more closely related to the type II than the type I PLA2 proteins, although it lacks the type-specific 6-residue C-terminal extension. The sequence of the cDNA of this gene has been published. Chen, J., et al., 1994, J. BIOL. CHEM. 260: 2365–68, FIG. 1 (which is hereby incorporated by reference).

Figure 1:
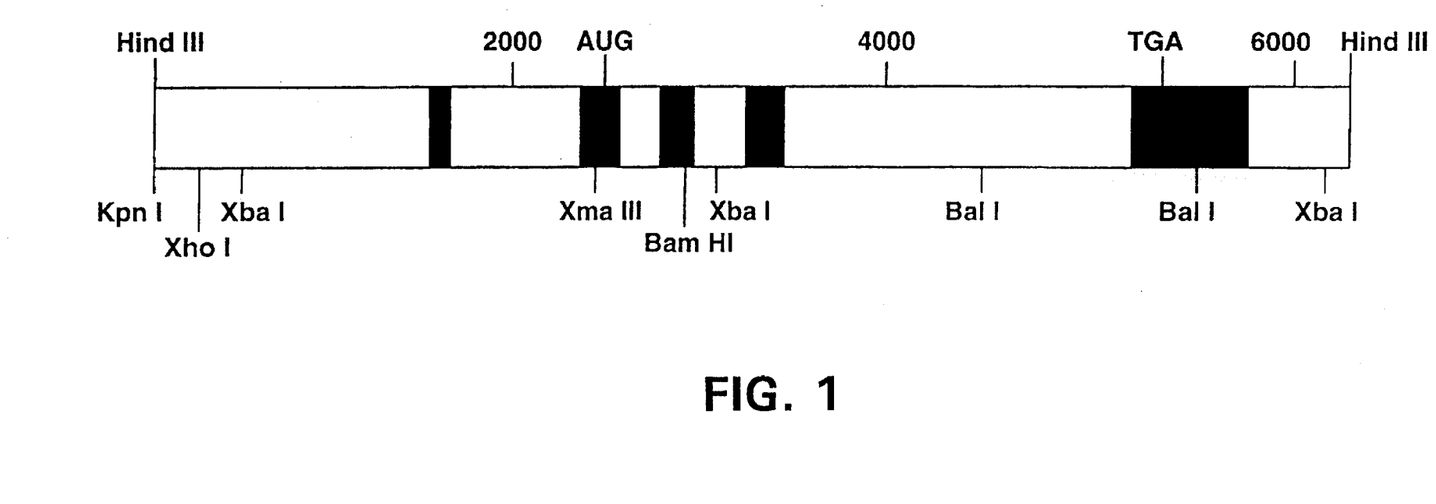
FIG. 1 is a diagrammatic representation of the human Type II Phospholipase A2 gene fragment used for the production of transgenic mice and rats.

The full length hnp-II-PLA2 gene consists of a 5' untranslated exon and 4 coding exons. A 6.2 Kb Hind III fragment can be isolated from normal human DNA, that contains the full length gene and about 750 bp 5' of the 5' cap site, which includes a promoter, may be isolated by means of synthetic oligonucleotides constructed according to the published sequence. A restriction map of the hnp-II-PLA2 is shown in FIG. 1. It is anticipated that transgenic mice or rats having any type II PLA2 gene from any mammal will have substantially the same phenotype as the transgenic mice and rats described in the working example below. The preferred embodiment is a transgenic animal having hnp-II-PLA2 because this particular isozyme is most relevant to the inflammatory process of humans.

5.2 Construction and Characterization of Trangenic Animals Having Human Non-Pancreatic PLA-2

Animals of any species, including but not limited to mice, rats, rabbits, guinea pigs, pigs, micro-pigs, and non-human primates, e.g., baboons, squirrel monkeys and chimpanzees, can be used to generate the transgenic animals of the invention. The preferred embodiments employ mice and rats.

Any technique known in the art can be used to introduce the 6.2 Kb Hind III fragment containing the hnp-II-PLA2 gene into animals to produce the lines of transgenic animals. Such techniques include, but are not limited to pronuclear microinjection (Gordon et al., 1980, PROC. NATL. ACAD. SCI. USA 77: 7380–7384; Gordon & Ruddle, 1981, SCIENCE 214: 1244–1246; U.S. Pat. No. 4,873,191 to T. E. Wagner and P. C. Hoppe); retrovirus mediated gene transfer into germ lines (Van der Putten et al., 1985, PROC. NATL. ACAD. SCI. USA 82: 6148–6152); gene targeting in embryonic stem cells (Thompson et al., 1989, CELL 56: 313–321);

electroporation of embryos (Lo, 1983, MOL. CELL. BIOL. 3: 1803–1814); and sperm-mediated gene transfer (Lavitrano et al., 1989, CELL 57: 717–723); etc. For a review of such techniques, see Gordon, 1989, Transgenic Animals, INTL. REV. CYTOL. 115: 171–229. (Each of the above-references is incorporated by reference herein in their entirety).

Once the founder animals are produced, they can be bred, inbred, crossbred or outbred to produce colonies of animals of the present invention. Generally inbred animals, having twice the number of hnp-II-PLA2 genes will have accordingly higher levels of hnp-II-PLA2 in all tissues The present invention provides for transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail.

The successful expression of the transgene can be detected by any of several means well known to those skilled in the art. Non-limiting examples are Northern blot of mRNA isolated from skin, lung, liver or kidney, enzyme assay of homogenates of the tissues in Which the transgene is most strongly expressed, i.e., liver, lung, kidney and skin or of serum and gross examination for the characteristic alopecia, runting or dermatitis.

Figure 3:
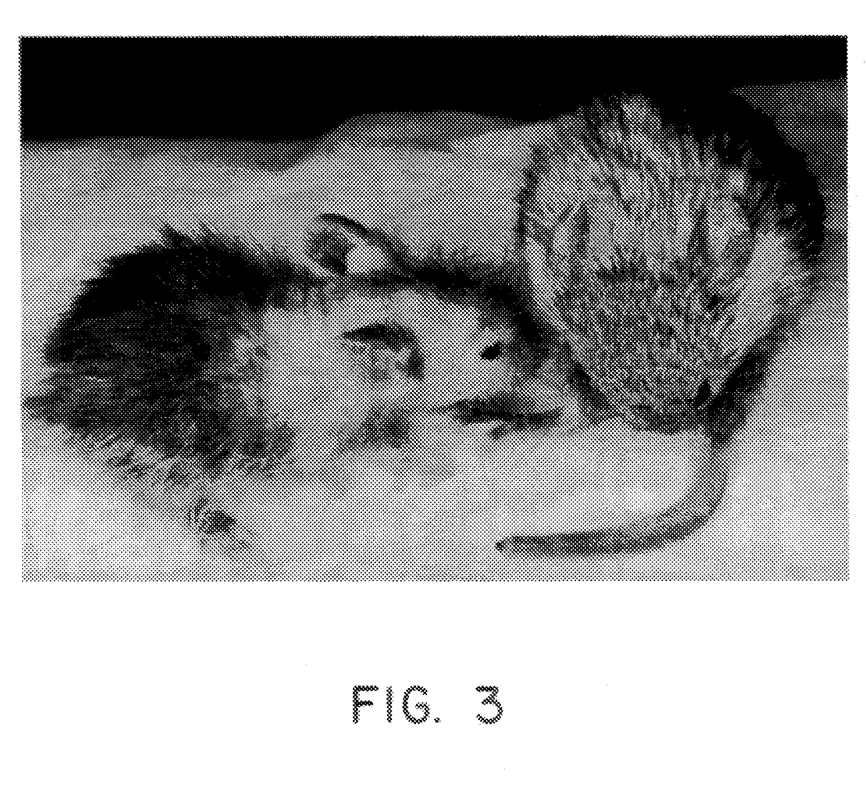
FIG. 3 is a photograph of 17 day old human type II PLA2 founder #854 and a non-transgenic littermate. The transgenic mouse (top) displays severe hair loss around the head.
Figure 4:
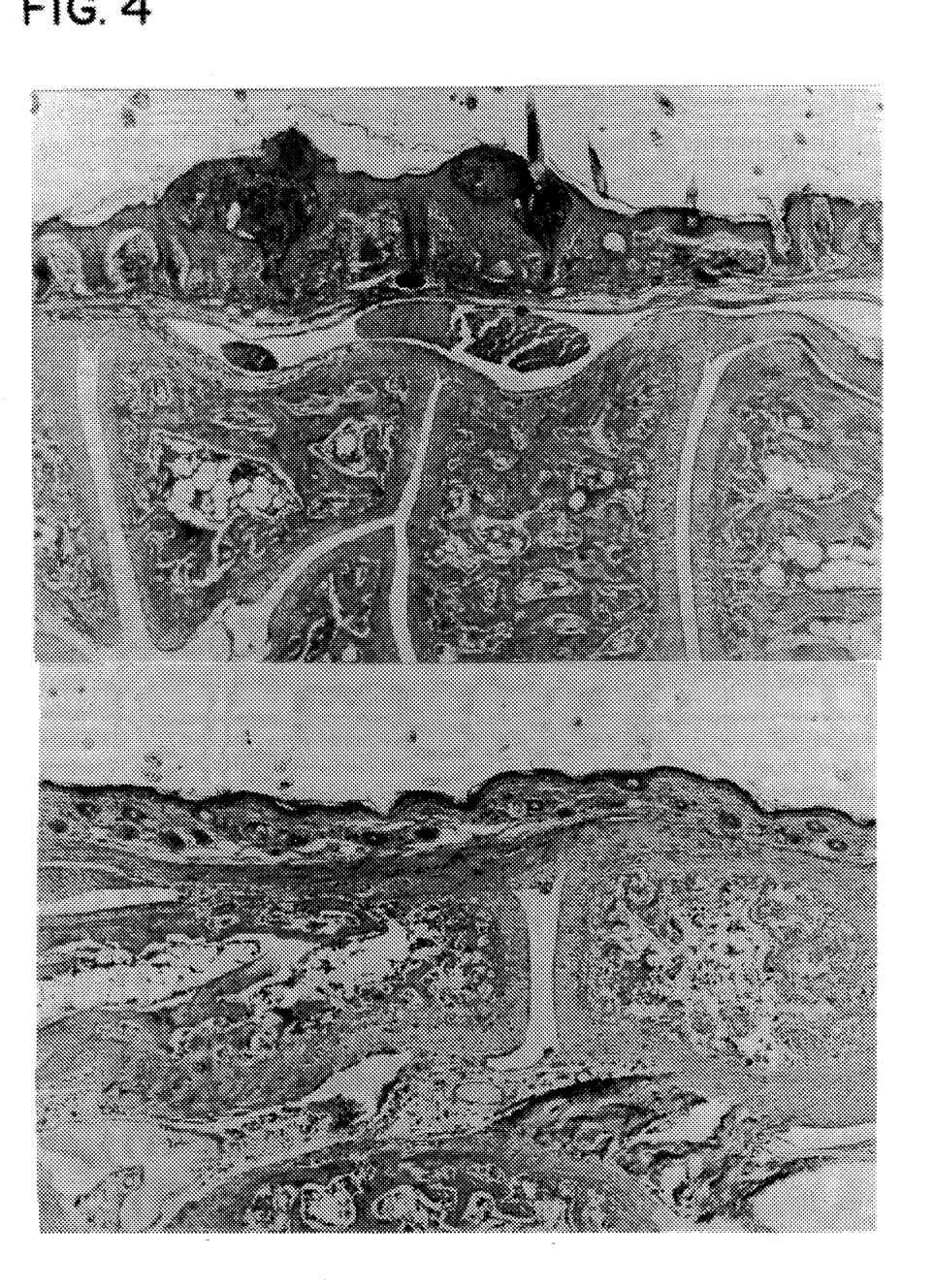
FIG. 4 is a photograph of Hematoxylin and Eosin stained sections of the paw of 19 day transgenic mouse (top) and a photograph of a similar Hematoxylin and Eosin stained sections from the skin of 19 day old non-transgenic littermate (bottom) showing epidermal and adnexal hyperplasia and adipocyte atrophy.

The transgenic animals of the present invention display multiple biochemical and physical signs that are attributable to the effects of the transgene. The gross signs presented by these animals include a delayed onset of the "adolescent growth spurt" and a reduction in the acceleration of the rate of growth at the time of its onset. See FIG. 2 which shows the bi-weekly weight of a representative transgenic and of a normal littermate. This results in an apparently transient "runting syndrome". There is a fluctuating alopecia that varies from near complete to moderate alopecia, see FIG. 3, associated with a exfoliative, hyperkeratotic dermatitis. Histological signs of the transgene are concentrated in the dermis where adnexal and epidermal hyperplasia predominate as are shown in FIG. 4.

Figure 5:
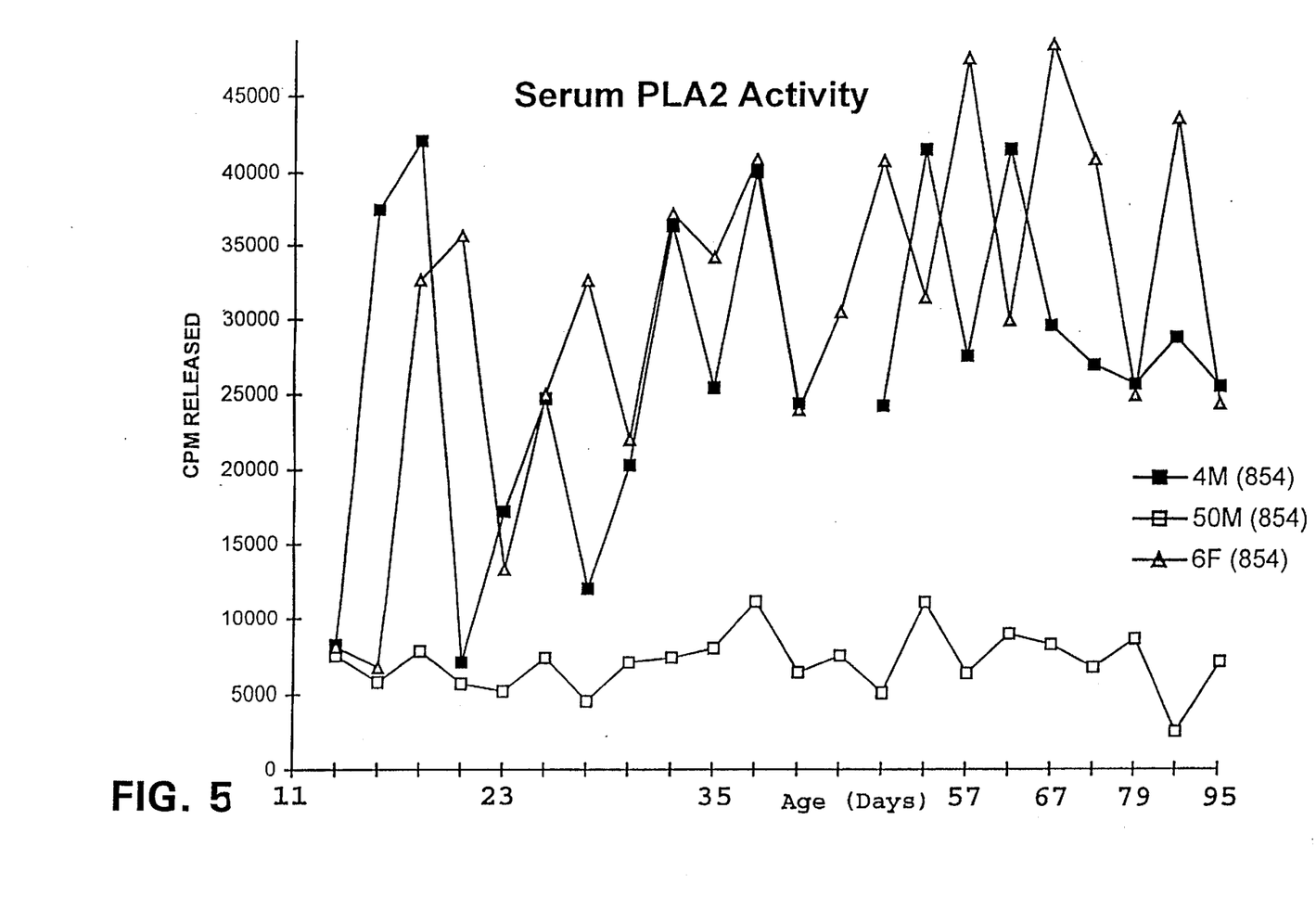
FIG. 5 shows the average level of serum PLA2 activity in Phospholipase A2 transgenic mice and non-transgenic littermates from birth to adulthood.

The primary biochemical abnormality of the transgenic animals is an elevated level of phospholipase $A_2$ activity in the serum. The elevated levels vary between about twice normal and about ten fold above normal. FIG. 5. Uncommonly, animals will be seen with serum levels nearly 20 fold above normal. The tissue of origin of this protein can be determined at the time of sacrifice by Northern blot of the organs. Such blots show expression of human type II PLA2 mRNA can be observed in liver, lung, skin and kidney but that it is present in low levels if not absent from the gonads, brain, heart and lymphoid organs.

Physiologically expressed hnp-II-PLA2 is secreted. However, the enzyme is sufficiently lipophilic so that much of the secreted enzyme remains associated with the cell of origin under non-pathologic conditions. Very high levels of PLA2 activity in the serum are found in subjects having severe medical diseases. Serum PLA2 activity is markedly elevated in patients with Gram negative septic shock. In one trial, serum PLA2 activity was increased 16-fold compared to healthy individuals (P. Vadas, J. Lab Clin. Med. 104: 873, 1984). The level of serum PLA2 activity correlates directly with the magnitude and duration of the circulatory collapse observed in patients with gram-negative septic shock (Vadas, P., et al., 1988, CRIT. CARE MED. 16: 1) and is thought to be a contributing factor in the development of hypotension in septic shock. Consistent with this data, infusion of PLA2 can mimic many of the hemodynamic effects of septic shock (Green et al., 1991, INFLAMMATION 15: 355).

Patients with gram-negative septic shock and concurrent adult respiratory distress syndrome (ARDS) have a mean serum PLA2 activity 20 fold greater than controls and 44% higher than septic shock patients without ARDS (P. Vadas, J. Lab. Clin. Med. 104: 873, 1984) and PLA2 activity has been identified in bronchoalveolar lavage fluid of patients with ARDS (Offenstadt et al. Intensive Care Med. 7: 285, 1981). In experimental animal models, infusion of PLA2 in dogs resulted in a respiratory distress syndrome similar to adult ARDS and lung microsomal PLA2 activity has been shown to be increased in septic shock in rats (Von Wichert et al., Biochim. Biophys. Acta 664: 487, 1981). Chronic levels of PLA2 activity in excess of 50 fold above normal are, thus, likely to be incompatible with health and fertility. Thus, in a preferred embodiment the transgenic animals of the invention have a serum PLA2 levels between about twice and 50 time that of their non-transgenic counterparts and in a more preferred embodiment the transgenic animal has levels between 2 fold and 20 fold above normal.

5.3 Use of the Transgenic Animals

The present invention can be used to determine the effectiveness of a test compound as a potential inhibitor of PLA2 activity, and particularly of human platelet PLA2 activity. The animals can be administered the test compound, in a pharmaceutically acceptable form, at varying doses and intervals, the determination of which is routine for those skilled in the art.

The effectiveness of the test compound may be determined by the examination of the characteristic features of the test animals noted above. Thus, the administration of therapeutically effective test compounds will be associated with decreased levels of tissue or serum PLA2 activity, increased pelage and the remission of the histologic abnormalities seen in the skin. In addition, when the study is conducted during the growth spurt period of the animal, there will be seen a return of body weight towards the norm.

The animals of the invention are useful for identifying inhibitors of human phospholipase A2 that have in vivo activity and for selecting compounds for testing in human clinical trials for the treatment of a variety of human pathological conditions wherein the abatement of unwanted inflammation is indicated. The selection of the dose of the compound thus discovered can be guided by pharmacologic principles well known to practitioners skilled in the art. The range of the appropriate dose for the beginning trial is scaled according to the ratio of the surface area of the test animal to the surface area of the human subject in need or treatment. Alternatively, dosages may be scaled according to the ⅔ power of the ratio of the body weights.

Disease conditions the treatment of which PLA2 inhibitors are expected to be useful include: the arthritides, especially rheumatoid arthritis; skin diseases such as psoriasis, pemphigus and bullous pemphigoid; systemic inflammatory response syndrome (Fink, M. P., 1993, CRITICAL CARE MED. 21: 957) such as seen in septic shock; and in certain chronic diseases that have been associated with increased levels of PLA2, e.g., schizophrenia (Noponen, M., 1993, BIOL.PSYCHIATRY 34: 641) and Crohn's Disease (Minami, T., et al., 1992, GUT 33: 914), or where PLA2 activity is implicated in the pathophysiology, e.g., atherosclerosis.

The animals of the invention can be used to investigate two types of compounds that negatively effect the expression or activity of PLA2. A potential inhibitor can function, at the protein level, as a competitive or non-competitive inhibitor of the enzyme. Alternatively, an antagonist functions at the transcriptional or translational level to inhibit the synthesis of the PLA2 protein. Such antagonists, of course, can not be detected in an in vitro assay.

The animals of the present invention can also be used to implement several, well characterized animal disease models of inflammation. The increased concentration of PLA2 in the animals of the invention provides an increased sensitivity of these test models to the effects of PLA2 inhibitors. These models include, by way of illustration, models of rheumatoid arthritis: See, e.g., publications by Lehman, T. J. A. (*Lactobacillus casei* induced arthritis in rats); Whitehouse, M. W. (adjuvant arthritis in rats); Wilder, R. T. (streptococcal cell wall induced arthritis in rats); and Cremer, M. (type II collagen induced arthritis in rats and mice) in CRC HANDBOOK OF ANIMAL MODELS OF RHEUMATIC DISEASES, ed. by Greenwald and Diamond, H. S., 1988, CRC Press, Boca Raton, Fla. Further examples showing research using rat models of sepsis and related conditions can be found in: Mancuso, G., et al., 1994, INFECT. IMMUN. 62: 2748–53; Wesuy, S., et al. , 1994, FREE RADIC. BIOL. MED. 16: 445–51; Ribeiro, S. P., et al., 1994, CRIT. CARE MED. 22: 922–929; Hotchkiss, R. S., et al., 1994, PROC. NATL. ACAD. SCI. 91: 3039–43; Eastridge, B. J., et al., 1994, ANN. SURG. 219: 298–305; and Irika, K., et al., 1994, J. SURG. RES. 56: 216–20. Examples of mice used for the same types of investigation are found in: Firestone, G. S., et al., 1994, J.IMMUNOL. 52: 5853–59; Miles, R. U., et al., 1994, J. TRAUMA 36: 607–611; Neely, A. N., et al., 1994, INFECT. IMMUN. 62: 2158–64; Suittors, A. J., et al., 1994, J. EXP. MED. 179: 849–56. (each of the above-noted publications is herewith incorporated by reference).

5.4 High Molecular Weight Phospholipase $A_2$ Ttansgenic Animals

The invention also encompasses transgenic animals that express abnormal levels of the cytosolic high molecular weight PLA2 (cPLA2). Transgenic animals that over express the human cPLA2 gene can be used to identify inhibitors and antagonists of cPLA2 in the same manner as is described above. The cPLA2 enzyme is considered to contribute to the production of leukotrienes and prostaglandins. Thus, antagonists and inhibitors of cPLA2 will be useful in treating the same disease entities as are noted herein above for the low molecular weight PLA2 inhibitors and antagonists.

The cloning and sequencing of the human cPLA2 cDNA has been described. Clark, J. D., et al., 1991, CELL 65: 1043–51; Sharp, J. D., et al., 1991, J.BIOL.CHEM. 266: 14850–53. The sequence of the cPLA2 cDNA is given in FIGS. 1 of those publications which are herewith incorporated by reference. The transgenic animal can be constructed by insertion of the cPLA2 cDNA into an expression vector and expressing the cPLA2 gene operably linked to-a strong exogenous promoter. Alternatively, the full length genomic clone can be obtained by use of the cDNA using techniques well known to those skilled in the art.

The transgenic animals expressing the cPLA2 gene can be identified by measuring the level of cPLA2 mRNA and by measurement of the levels of enzyme activity as described above except that the $Ca^{++}$ levels must be controlled by a $Ca^{++}$/EGTA calcium buffer so that the free calcium levels are of the order of 1 µM. A buffer of 0.975 mM $Ca^{++}$ and 1.00 mM EGTA is suitable.

6. EXAMPLES

6.1 Production and Analysis of Transgenic Mice

The 6.2 Kb Hind III genomic fragment containing the human type II PLA2 gene (FIG. 1) was microinjected into the more visible (paternal) pronuclei of fertilized mouse oocytes essentially as described in Wagner and Hoppe, U.S. Pat. No. 4,873,191. From an initial session of microinjection, eight mice were identified as integration positive for the type II PLA2 gene by Southern blot analysis.

Figure 2:
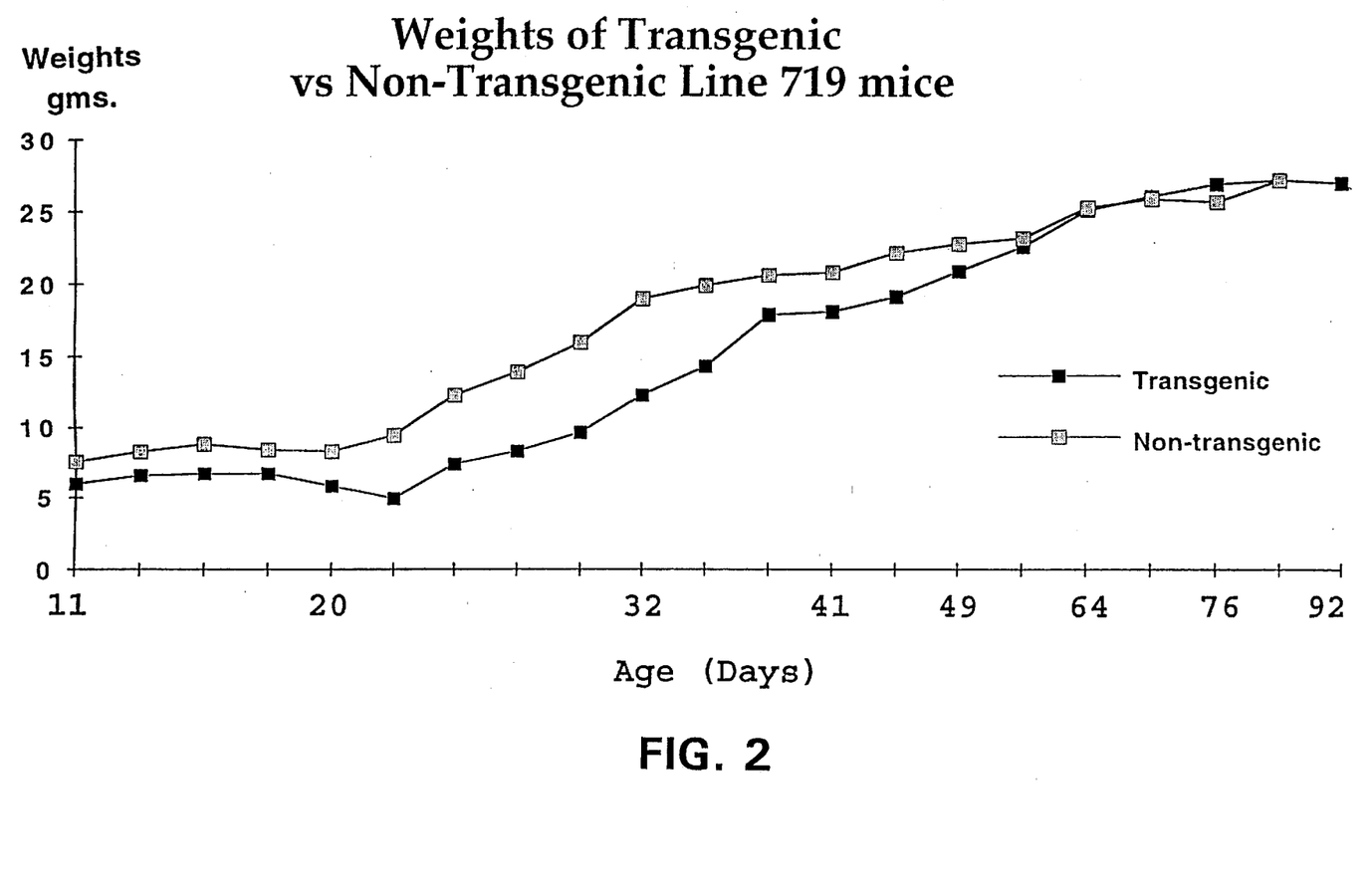
FIG. 2 shows a graph of the body weights of representative transgenic and non-transgenic mice from the same litter.

Seven of these eight "founder" transgenic mice shared a common phenotype upon gross observation. The transgenic mice looked normal during the first 7 days of age, 7 of the 8 mice developed, starting at one week of age, a dull and sparse pelage. (FIG. 3). This phenotype progressed until, at age 21 days, the most severely affected lines had developed severe alopecia and weighted roughly 30% less than normal littermates (FIG. 2). Subsequently, usually be one month of age, the affected mice reinitiate hair growth and then progress through periods relapse and remission of hair loss with an overall trend towards more severe alopecia.

Other gross observables include periorbital swelling and lethargy between 2 and 3 weeks of age. Adult mice also had noticeably swollen hind paws compared to their non-transgenic littermates. Of the seven founders that were mated to produce offspring (G1), five transmitted the gene and phenotype to their progeny.

6.1.1 Northern Blot Analysis of HNP-II-PLA2 Expression

Figure 6:
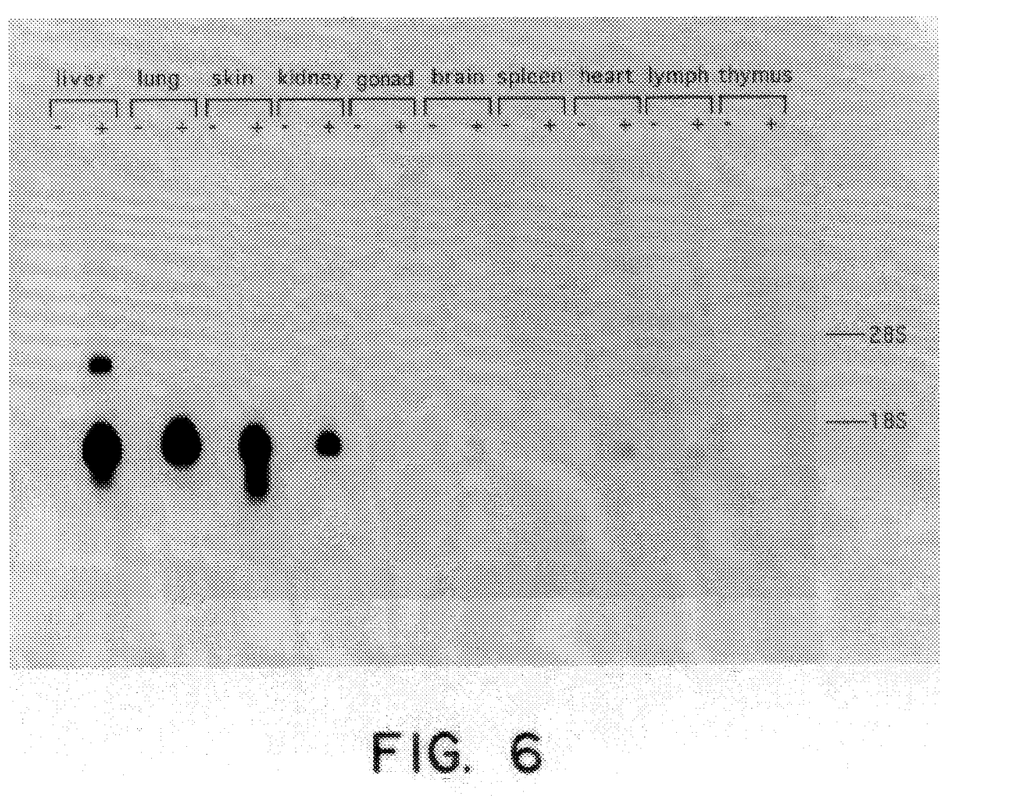
FIG. 6 is a photocopy of an autoradiograph of a Northern blot showing the tissue distribution of human Phospholipase A2 mRNA in transgenic mice.

To examine the expression of the human type II PLA2 gene in these mice northern blot analysis was performed using an 800 Kb human type II PLA2 cDNA fragment. Analysis was performed on 21 day old animals (the time of greatest severity of phenotype). Offspring from three founders were examined. As shown in FIG. 6, a 1.5 Kb PLA2 RNA was detected in the liver, skin, kidney, and lung. Although variability was observed between different transgenic lines, generally the highest level of RNA was observed in liver, followed by skin, kidney and lung. A lower level of expression was generally observed in the heart and lymph nodes.

6.1.2 Assays of PLA2 Enzymatic Activity

Serum assays of PLA2 activity were performed essentially as described by Davidson F. F., et al., 1990, J. Biol. Chem. 265: 5602–09, using [$^3$H]-oleic acid labeled *E. coli*. The reaction mixture consisted of 2 µL of serum, 100,000 cpm of [$^3$H]-oleic-acid-labeled, autoclaved *E. coli*, 100 mM Tris (pH=7.5) and 1 mM $CaCl_2$ in a final volume of 200 µL. The reactions were performed at 37° C. and the times adjusted to give between 7.5% and 20% hydrolysis of substrate lipid (generally 15 to 30 minutes). The reactions were terminated by the addition of 100 µL of 2M HCl followed by 100 µL of 20 mg/ml fatty acid free bovine serum albumin. The tubes were vortexed and centrifuged at 14,000×g for 5 min to remove bacteria. [$^3$H]-Oleic acid release was determined by scintillation counting of aliquots (330 µL) of the supernatant.

Phospholipase $A_2$ activity was measured in serum collected from both the affected mice and normal littermates to determine whether enhanced levels of PLA2 activity were present. A time course experiment was performed to determine whether the level of serum PLA2 activity varied during development and whether these changes could be correlated with the severity of the phenotype. Starting when the mice were 11 days old, the mice were bled 2 times a week until the mice were 8 weeks old. As shown in FIG. 5, PLA2 activity levels were uniformly elevated above the normal levels. Generally, PLA2 activity was 6 to 8 fold greater than that of the non-transgenic littermates.

6.1.3 Gross and Microscopic Examination at Necropsy

Because of the suspected role of PLA2 in inflammatory conditions and to ascertain the cause of swelling of the paws of the transgenic mice, histological examination of bone, fore and hind feet, liver, lung, spleen, thymus, pancreas, abdominal skin, forepaw skin, and hind foot skin were performed on animals between 16 or 21 days old from several different lines and the results were compared to normal littermates. The only pathology noted in these sections was found in the skin samples taken from the abdomen and back and the skin covering the forepaw and hind foot. In these sections there were epidermal and adnexal hyperplasia and hyperkeratosis (FIG. 4). The residual hair follicles in the skin of the transgenic mice appeared to be in the late catagen or telogen phase of the hair growth cycle suggesting the potential for additional future growth phases. The changes in the skins of the transgenic mice was proliferative rather than degenerative or atrophic.

Histological examination of transgenic mice between 3 and 6 months of age revealed focal inflammatory lesions in the feet, characterized by focal acute folliculitis (inflammation of individual hair follicles) and subacute interstitial inflammation (involving the deeper tissues between and adjacent to the bones of the foot. Ulcerations of the forepaw and skin of the neck were also observed. Skin lesions were accompanied by epidermal hyperplasia, inflammation of the dermis (subacute dermatitis) or dermal fibrosis. Many of the PLA2 transgenic mice had lymph nodes with an accumulation of plasma cells indicating antigen/ antibody response in the nodes.

In addition, most of the transgenic mice examined, had increased extramedullary hematopoiesis in the liver and spleen compared with non-transgenic mice. However, the presence of ulcerations with concurrent inflammation of the skin and foot can stimulate hematopoiesis, therefore, the extramedullary hematopoiesis could represent a non-specific effect of the chronic dermatitis, rather than a specific effect of the hnp-II-PLA2 expression.

6.2 Production and Analysis of Transgenic Rats

The 6.2 Kb Hind III genomic fragment containing the hnp-II-PLA2 gene was microinjected into male pronuclei of fertilized rat oocytes using similar procedures as described in Wagner and Hoppe, U.S. Pat. No. 4,873,191 with the following modifications. Three to four week old weanling Sprague-Dawley female rats were superovulated using pregnant mare serum gonadotropin (PMSG) and human chronic gonadotropin (HCG). PMSG was injected intraperitoneally at 11:00 AM on day −2 and HCG was injected intraperitoneally at 10:30 AM on day 0. Before administration of PMSG, the animals were weighed and the dose of each hormone was calculated by according by the following schedule: (wt/dose) <70 gr/10–12.5 IU; 70–80 gr/15 IU; 80–85 gr/17.5 IU; 90+gr/25 IU. After injection of the HCG, animals were placed with fertile Sprague-Dawley male rats with a proven mating record. Females were checked for copulation plugs at approximately 9:00 AM on day +1. Females not displaying a definite copulation plug were vaginal smeared to detect the presence of sperm. All animals identified as having mated were used as embryo donors.

Donor females were sacrificed one at a time and the oviducts were dissected into Dulbecco's Phosphate Buffered Saline (DPBS, Gibco-BRL) supplemented with 0.5 g bovine serum albumin (Sigma) and antibiotics. The DPBS was sterile filtered and maintained at 37° C. during the oviduct harvest. Oviducts were then placed into a standard mouse embryo culture media (BWW, Irvine Scientific, Santa Anna, Calif.). The BWW media was supplemented with BSA and antibiotics and Hyaluronidase (Sigma) at a concentration of 1.4 mg/ml. The ampulla section of the oviduct was incised and the cumulus masses extracted into the media for the removal of the cumulus cells from the embryos. The embryos remained in the Hyaluronidase media for 5 minutes or less at 37° C. Embryos were then collected and washed 3 times in the BWW media (without hyaluronidase) and placed into 50 ul droplets of BWW media and covered with heavy paraffin oil (Sigma) to prevent evaporation of the media droplets. 35 mm culture dishes (Corning) were used for the culture of the embryos. Embryos were then incubated at 37° C. in 5% $CO_2$, 5% $O_2$, and 90% $N_2$ for subsequent microinjection.

Embryos were placed into 15 ul microdroplets of hepes buffered BWW media (Irvine Scientific) on a depression slide covered with heavy paraffin oil. Generally, 20 to 30 embryos were placed on a slide for microinjection. Care was taken to minimize the time embryos were exposed to the hepes media to reduce adverse effects which can be caused by the hepes. In comparison to superovulated mouse embryos, the rat embryos displayed an increased developmental diversity. In addition, some of the rat embryos displayed what would be described as a distorted morphological appearance. On the average, 58% of harvested embryos presented suitable pronuclei for microinjection. After completion of injecting the embryos, they were washed 3 times in the non-hepes buffered BWW media and incubated in microdroplets until they were transferred into recipient females.

Adult Long-Evans rats, >8 weeks of age, were used as recipients of injected embryos. A unilateral pregnancy was achieved by a brief surgical procedure involving the "peeling" away of the bursa membrane on the left uterine horn as described by Vanderhydet et al., 1986. The surgery took place 1 to 6 weeks before embryo transfer. This procedure allows for endogenous embryos to develop on the intact uterine horn thus increasing the chances of the recipient female rat maintaining a pregnancy. Injected embryos were transferred to the left uterine horn via the infundibulum. Potential transgenic founders (Sprague-Dawley albino pups) can be identified immediately at birth from the endogenous litter mates (Long-Evans pigmented pups) allowing for prompt feedback with respect to experimental litter sizes. In addition, recipient females were synchronized using GNRH agonist (GnRH-a): des-gly$^{10}$, (D-Ala$^6$)-LH-RH Ethylamide, Sigma Chemical Co.,St. Louis, Mo. The GnRH-a was diluted to a concentration of 200 ug/ml in 0.9% saline. Potential recipient females received 40 ug in 0.2 ml injected intraperitoneally on day −4. Females were then mated to fertile males on day 0. On the morning of day +1, potential recipients were checked for a vaginal plug. If there was no indication of mating, a vaginal smear was done to check for the presence of sperm. All females identified as having mated, became available for embryo transfer.

Four transgenic rats, containing the human type II PLA2 gene, were identified by Southern blotting and PCR analysis. Two of these transgenic rats displayed a common grossly observable abnormal phenotype after the first several weeks of age, consisting of a light pelage on the back of the head. The transgenic offspring of these animals developed a remarkably similar phenotype to that observed in the above-described transgenic mice. By three weeks of age, the rats exhibited the most severe alopecia, periorbital swelling and an exfoliative dermatitis that was most prominent on the tail. Transgenic rats also displayed the same delayed and attenuated growth spurt as were observed in the transgenic mice. As with the mice the severity of the gross pathology phenotype varied continuously throughout their adult life.

We claim:

1. A mouse or rat expressing a transgene encoding non-pancreatic, low molecular weight phospholipase $A_2$ so that the serum phospholipase $A_2$ activity, as determined by hydrolysis of oleic acid-labelled *E. coli* lipids, is increased relative to a normal animal of the same species, wherein said mouse or rat displays a pathologic phenotype selected from the group consisting of adnexal hyperplasia, alopecia, exfoliative dermatitis and hyperkeratosis.

2. The mouse or rat of claim 1 wherein the serum phospholipase $A_2$ activity is about 2 fold to about 50 fold above the level of a normal animal of the same species.

3. The mouse or rat of claim 2 wherein the transgene is a human non-pancreatic, low molecular weight phospholipase $A_2$ gene.

4. The mouse or rat of claim 3 wherein the transgene is hnp-II-PLA2.

5. A method of investigating a test compound to determine its efficacy as an antagonist or inhibitor of phospholipase $A_2$, comprising the steps of:
   a. administering a test compound to a transgenic mouse or rat of claim 1;
   b. measuring the level of phospholipase $A_2$ activity in a sample of the serum of said mouse or rat; and
   c. comparing the measured phospholipase $A_2$ activity level to the level of a sample of the serum of a normal animal of the same species.

6. The method of claim 5 wherein the transgene is hnp-II-PLA2.

7. A method of investigating a test compound to determine its efficacy as an antagonist or inhibitor of phospholipase $A_2$, comprising the steps of:
   a. administering a test compound to a transgenic mouse or rat, said mouse or rat expressing a transgene encoding non-pancreatic, low molecular weight phospholipase $A_2$ so that the serum phospholipase $A_2$ activity, as determined by hydrolysis of oleic acid-labelled *E. coli* lipids, is increased relative to a normal animal of the same species, wherein said mouse or rat displays a pathologic phenotype selected from the group consisting of adnexal hyperplasia, alopecia, exfoliative dermatitis and hyperkeratosis;
   b. observing said mouse or rat; and
   c. comparing said mouse or rat to transgenic animals of the same genotype absent the test compound to determine the presence or absence of the pathologic phenotype.

8. The method of claim 7 wherein the transgene is hnp-II-PLA2.

9. The method of claim 7 which further comprises the steps of biopsying or necropsying said mouse or rat so that a specimen is obtained and examining the specimen from said mouse or rat to determine the presence or absence of the sign.

10. The method of claim 9 wherein the transgene is hnp-II-PLA2.

* * * * *